United States Patent [19]

Fischell

[11] 4,275,739
[45] Jun. 30, 1981

[54] CHARGE CONTROL SWITCH RESPONSIVE TO CELL CASING DEFLECTION

[75] Inventor: Robert E. Fischell, Silver Spring, Md.

[73] Assignee: The Johns Hopkins University, Baltimore, Md.

[21] Appl. No.: 6,723

[22] Filed: Jan. 26, 1979

[51] Int. Cl.³ .............................................. A61N 1/36
[52] U.S. Cl. .................................. 128/419 PS; 320/46
[58] Field of Search ................... 128/419 PS; 320/43, 320/46, 48, 52; 340/591, 592, 593, 611, 626, 632, 636; 429/61, 90, 91, 93, 163

[56] References Cited

U.S. PATENT DOCUMENTS

| 3,003,100 | 10/1961 | Euwema | 320/46 |
| 3,100,862 | 8/1963 | Collier | 320/46 |
| 4,082,097 | 4/1978 | Mann et al. | 128/419 PS |

Primary Examiner—William E. Kamm
Attorney, Agent, or Firm—Robert E. Archibald

[57] ABSTRACT

A switch structure, adapted for sensing the state-of-charge of a rechargeable cell, includes a contact element which detects cell casing deflection that occurs as a result of an increase in gaseous pressure within the cell when the cell is returned to its fully charged state during a recharging operation.

7 Claims, 6 Drawing Figures

CHARGE CONTROL SWITCH RESPONSIVE TO CELL CASING DEFLECTION

STATEMENT OF GOVERNMENTAL INTEREST

The invention described herein was made in the performance of work under a NASA 5-23732 contract and is subject to the provisions of Section 305 of the National Aeronautics and Space Act of 1958, Public Law 85–568 (72 Stat. 435; 42 U.S.C. 2457).

BACKGROUND OF THE INVENTION

In the development of various types of implantable biomedical apparatus, such as cardiac pacemakers and other implantable body tissue stimulators, it has previously been proposed that a rechargeable battery or cell be utilized to supply operating energy to the remaining circuitry of the implanted unit. By way of examples, in my earlier issued U.S. Pat. Nos. 3,867,950; 3,888,260; and, 4,096,866, I disclosed the use of a rechargeable nickel-cadmium cell for supplying operating energy to implantable cardiac pacemaker and tissue stimulator circuitry. As disclosed in these prior patents, the use of such a rechargeable battery is intended to obviate the necessity of having to replace depleted batteries, as often occurs when non-rechargeable type batteries are employed for such implantable application.

The need remains, however, to improve the control of the recharging operation for such an implanted rechargeable cell, in order to assure that the recharging operation is performed in an efficient, yet safe manner. If has previously been proposed, for example, to provide a means for sensing when a rechargeable battery, such as the nickel-cadmium cell, has been returned to its fully charged condition, during a recharging operation, for controlling the recharger in such a manner as to discontinue charging when full-charge state is achieved. As pointed out by Frezzolini et al in their U.S. Pat. No. 3,775,661, nickel-cadmium cells produce no discernible repetitive voltage characteristics, thus making battery potential a relatively ineffective state-of-charge indicator for use in controlling the re-charging operation. Instead, this prior art suggests that a better indication of the state-of-charge of a nickel-cadmium cell is the increase in gaseous pressure within the cell casing which enclose the chemical elements of the battery, produced by the buildup of oxygen therein when the cell is returned to its fully charged state. Frezzolini et al, however, require the provision of a vent or aperture through the cell casing which communicates internal cell pressure build-up with a resilient diaphragm disposed in a control unit mounted external to the battery. As the pressure within the cell casing increases, the diaphragm is flexed to actuate an associated switch connected in the battery charging circuitry, so as to de-energize the charger when the battery internal pressure indicates a return to the fully charged state.

SUMMARY OF THE INVENTION

In accordance with the present invention, it is also proposed to utilize the increased oxygen pressure within the nickel-cadmium rechargeable cell, as a control indication that the cell is in its fully charged state; e.g. in order to control the recharging circuitry in order to decrease the recharging current, either to zero or to a predetermined safe trickle value, depending upon the requirements of practice. However, in contradistinction to the teachings of the prior art, it is proposed in accordance with the present invention to accomplish the sensing of the pressure build-up within the rechargeable cell, by sensing deflection of the cell casing itself, rather than requiring that the casing be provided with an opening, as taught by Frezzolini et al, to communicate the internal cell pressure to an external sensing diaphragm. As a result, the present invention maintains the casisng intact and thus preserves the hermetic seal between the interior of the cell and its surroundings in vivo.

In accordance with the present invention, the deflection of the cell casing produced by the increasing pressure within the rechargeable cell is sensed by mounting an electrical contact element adjacent the cell casing, such that the casing moves into contact with the contact element when the casing deflects an amount indicative that the cell has returned to its fully charged condition or state. When this control indication occurs, the cell recharging circuitry may be controlled to reduce the recharging current, in order to avoid overcharging the cell.

Accordingly, an object of the present invention is to provide a means for detecting when a hermetically sealed, rechargeable cell, of the type used for powering implantable biomedical devices, has been returned to a fully charged condition during a recharging operation, by sensing the build-up of internal cell pressure in a manner that preserves the cell's hermetic seal.

A further object of the present invention is to provide a means for sensing the fully charged condition of a rechargeable nickel-cadmium cell, by sensing the deflection of the cell casing produced by the increase in internal oxygen pressure which accompanies a return of the cell to a fully charged condition.

A further object of the present invention is to provide a switch structure, of relatively simple design and construction, which reliably senses the deflection of the casing of a rechargeable electric power cell, as an indication of the state-of-charge of the cell.

Other objects, purposes and characteristic features of the present invention will, in part, be pointed out as the description of the present invention progresses and, in part, be obvious from the accompanying drawings wherein.

Figure 1:
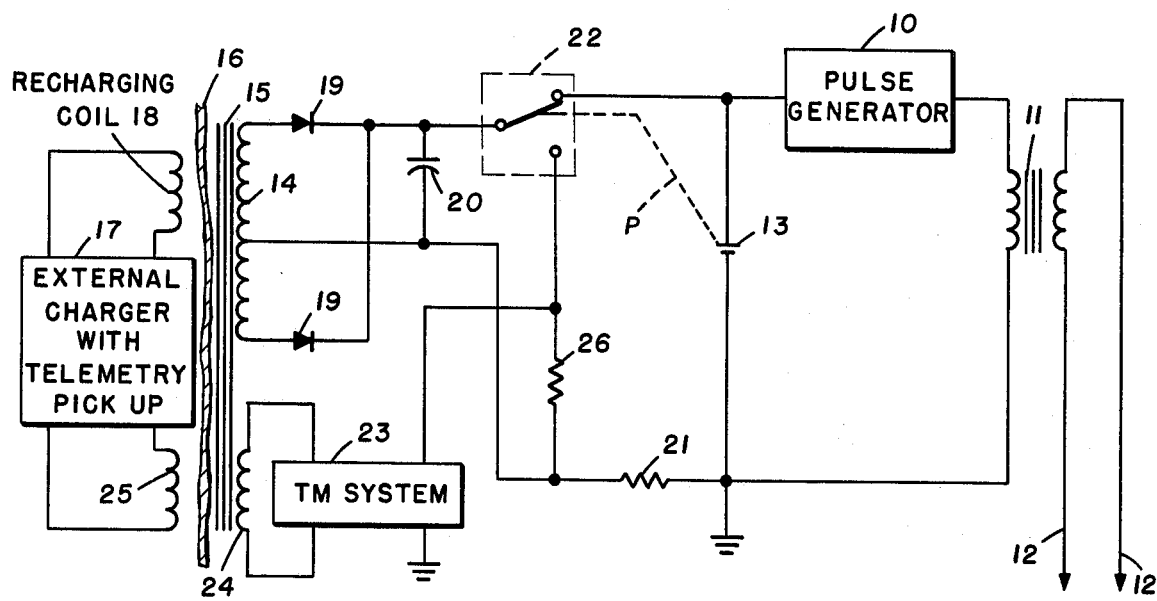
FIG. 1 is a simplified schematic diagram of an implantable tissue stimulator system powered by a rechargeable cell, to which the switch structure proposed in accordance with the present invention can be applied.

Referring now to FIG. 1 of the drawings, the proposed switch structure of the present invention is adapted for use in an implantable biomedical system, such as the illustrated tissue stimulator, which receives operating energy from a power cell or battery of the rechargeable type; e.g. the well-known nickel-cadmium cell. As shown, the tissue stimulator system is conventional and includes a suitable pulse generator 10 whose output pulses are applied to the selected body tissue of the patient by means of a transformer 11 which couples or connects the output of the generator 10 to suitable stimulation electrodes 12 connected to the heart or other body tissue to be electrically stimulated.

The pulse generator 10 receives its operating energy or supply voltage from a rechargeable battery, indicated at 13, which may be of the nickel-cadmium type, for example. The rechargeable cell 13 is recharged, as necessary, by means of a pick-up coil 14 which is wound on a suitable ferrite core 15 to inductively receive, through the skin 16 of the patient, recharging energy supplied by the external charger unit 17. This recharging energy might typically be in the form of an alternating magnetic field; e.g., at twenty-five kilohertz, generated at recharging coil 18. More particularly, the magnetic charging field is inductively picked up at winding 14, is full-wave rectified by the diodes 19 and filtered by the capacitor 20, and then applied to the battery 13, via current limiting resistor 21 and recharging control switch 22 which will be described in more detail hereinafter.

A telemetry system generally designated at 23 is included in the implanted tissue stimulator apparatus and responds, as will be described hereinafter, to the state-of-charge condition of the battery 13 so as to transmit, via winding 24 on the ferrite core 15, a signal indicative of such battery state-of-charge. The external charger unit 17 is provided with a pick-up coil 25 which receives the telemetry signal transmitted at 24 and, in response thereto, the external charger 17 is controlled so as to shut off, or reduce to a low trickle value, the recharging energy inductively coupled to the internal winding 14.

In accordance with the present invention, the state-of-charge condition of the battery or cell 13, during the recharging operation, is detected by monitoring the increase in internal cell pressure which occurs when oxygen is generated at the commencement of an overcharge condition within the typical nickel-cadmium, rechargeable cell. This is diagrammatically indicated in FIG. 1, by the dashed line P extending between cell 13 and switching function 22 in the recharging circuitry for cell 13. Thus, after the battery 13 has been restored, during the recharging operation, to its full charge condition as indicated by the increased oxygen pressure within the cell 13, the switch 22 is controlled or operated to its lower contact position so that the battery 13 is now disconnected from the recharging coil 14 and the telemetry system 23 is now rendered effective, in response to current flow through resistor 26, to generate a suitable telemetry signal which is inductively coupled external to the body via windings 24 and 25 as an indication that the battery has been returned to its full charge state. This telemetry signal can be used to operate suitable control switching circuitry; e.g., including a relay or transistor switching circuit(s), to either turn off the external charger 17 or to reduce the recharging current to a preselected trickle value.

Figure 2:
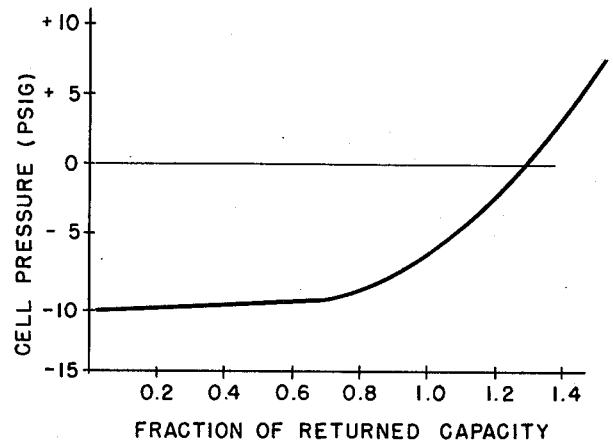
FIG. 2 is a graph illustrating how oxygen pressure varies typically as a function of the charge state for a rechargeable nickel-cadmium cell.

FIG. 2 illustrates, as previously noted, a typical curve of oxygen pressure versus returned state-of-charge for a nickel-cadmium cell during recharge. By actuating the switch 22 at a gauge pressure (psig) of approximately zero, the battery 13 would be disconnected from its recharging source at approximately 130% of returned capacity. This would prevent the nickel-cadmium cell from becoming permanently deformed and also help prevent any deformation of the external stimulator casing structure (not shown) which is typically employed in such implanted biomedical devices to hermetically seal the implanted unit against the infusion of corrosive body fluids.

Figure 3:
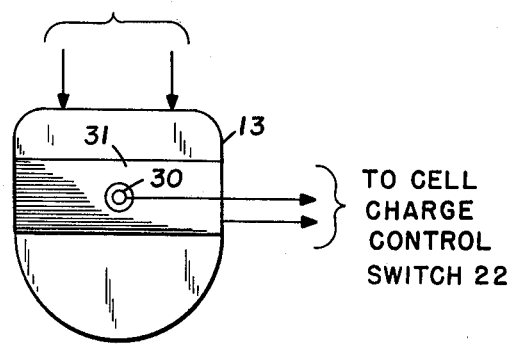
FIG. 3 and 4 illustrate a first embodiment of the switch structure proposed with the present invention.
Figure 4:
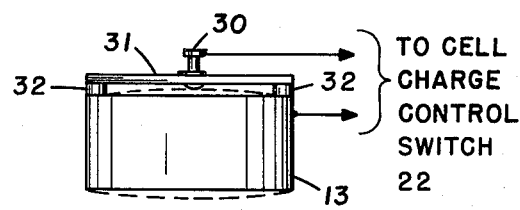

FIGS. 3 and 4 illustrate one embodiment of a switch structure for sensing pressure build-up within the rechargeable cell 13 upon return to its fully charged state, during a recharging operation, and for thereupon controlling the charge control switch 22 in FIG. 1 to decrease the amount of recharging current being supplied to the cell 13. More specifically, in this first embodiment of the present invention, a gold contact pin 30 is mounted on a substrate member 31 which is formed of suitable electrical insulating material, such as a sheet of epoxy glass, bonded by epoxy 32 to the side of the cell's metallic casing or can, with a predetermined spacing between the casing 13 and the contact pin 30. By way of example, it has been demonstrated in practice that for a 1 ampere-hour Ni-Cd cell being recharged at the 0.6 C rate, an outward casing deflection of approximately 0.001 inches occurs at about the 100 to 110% charge level; i.e. when the cell is in its fully charged state. Thus, during a typical recharging operation, when the recharging current being supplied to the cell 13, through the recharge control switch 22 in its illustrated position in FIG. 1, has returned the cell 13 to its fully charged condition, the cell casing will deflect outwardly, as represented in FIG. 4 by the dashed line, and make contact with the gold contact pin 30. When this occurs, the recharge control switching function 22 is controlled to its lower switching state to disconnect the cell 13 from the recharging source and to concurrently energize the telemetry system 23. As a result, a suitable telemetry signal is transmitted, via windings 24 and 25, to signal the external charger 17 that the cell 13 is fully recharged. Obviously, this detection performed by the switch structure 30–31 may be used for various other control/indication functions, as dictated by the requirements of practice; e.g. to actuate a visual indication to the patient that full recharge has been achieved.

It should also be understood at this time that the re-charge control switch 22 may take various forms, depending upon the requirements of practice: e.g. the single pole-double throw switching function 22 might be provided by conventional relay circuitry or well-known solid state switching circuits which respond to the shorting of the gold contact pin 30 to the battery casing 13 when the cell 13 has been returned to its fully charged condition.

Figure 5:
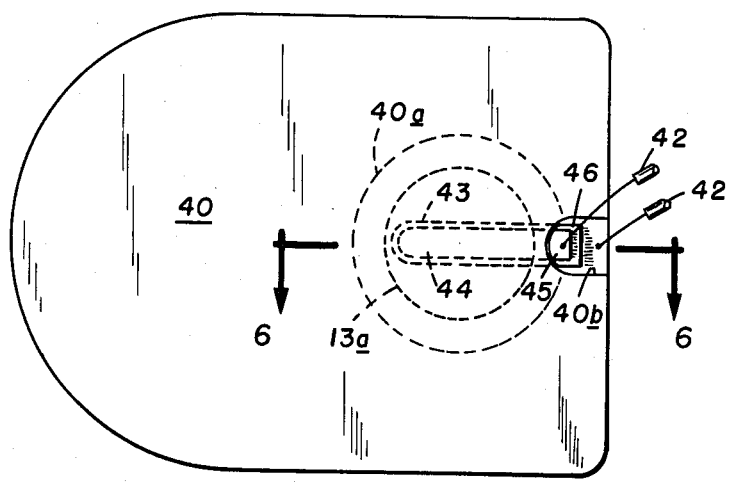
FIGS. 5 and 6 illustrate a second embodiment of the proposed switch structure.
Figure 6:
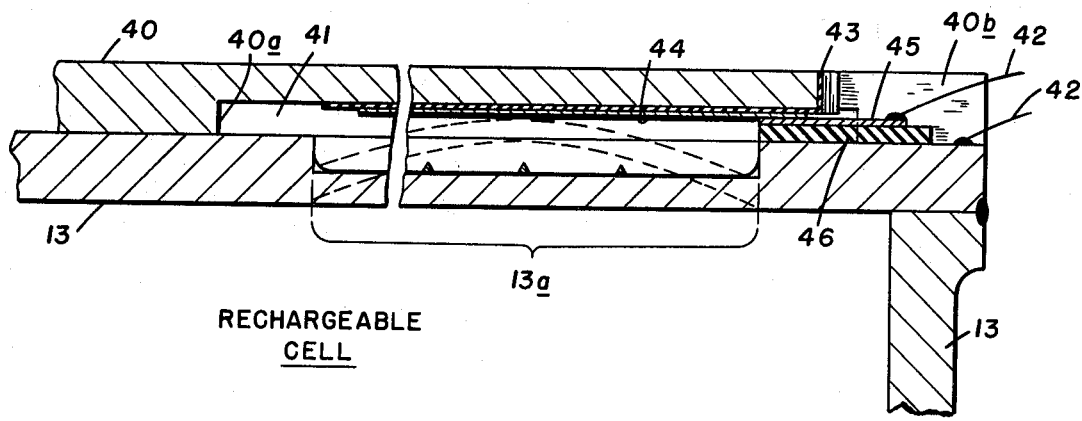

Referring now to FIGS. 5 and 6 of the drawings, a second embodiment of the proposed switch structure is shown mounted to the casing 13 of a rechargeable Ni-Cd cell of the type typically used to provide operating energy to implanted biomedical systems.

In this second embodiment, see FIG. 6, the upper wall of the cell casing 13 is provided with a circular recess forming a reduced thickness portion on the casing, designated at 13a. In one practical application of the proposed switching structure, the recessed portion 13a has a reduced thickness of approximately one-half of the 15 mil thickness of the typical nickel-cadmium metallic can or casing 13, to form a localized area at which the casing 13 will deflect outwardly when the internal oxygen pressure of the cell increases (see FIG. 2) upon return of the cell 13 to its fully charged state during recharge.

Overlying the cell casing 13 is a support or stiffener plate 40 fabricated of a structurally rigid material, such as steel. The plate 40 is formed with a circular recess 40a which overlies and surrounds the reduced portion 13a of the cell casing, so as to form a chamber 41 in communication with the reduced portion 13a. The stiffener plate 40 is also formed with a suitable U-shaped notch 40b at its right-hand end FIG. 5, defining an electrical connection location at which leads 42 can be connected to the switching structure to provide the control indication of when the oxygen pressure within the casing has increased to the point corresponding to a return of the battery to its fully charged state.

More specifically, a thin suitable pad 43 of electrical insulator material, such as a ceramic, extends along the underside of the recessed portion 40a in the stiffener plate 40 from the U-shaped access location and into the chamber 41 between the reduced portion 13a of the battery casing and the stiffener plate recess 40a. Mounted on this insulator pad 43 is a thin strip 44 of suitable conductor material; e.g. a gold alloy, which functions as the electrical contact member against which the casing portion 13a deflects into contact to indicate the fully charged condition of the cell. The right-hand end of the conductor strip 44 is extended out through the U-shaped access location 40b, for example by means of a connected conductor strip 45 of comparable width which, in turn, is mounted on top of a second insulator pad 46 secured to the upper surface of the battery casing 13.

In operation of the second embodiment of the proposed switching structure, when the rechargeable cell has been returned to its fully charged condition, by the recharging current supplied through the charge control switch 22 (see FIG. 1), the internal oxygen pressure of the cell will cause the reduced thickness portion 13a of the casing to deflect upwardly, as represented by the dashed lines in FIG. 6, so that it contacts the conductor strip 44 carried on the stiffener plate 40. If desired, to assure good electrical contact with the conductor strip 44, the upper surface of the recess 13a may be plated with gold and, in addition, be fabricated with sharpened points for enhancing electrical connection. As shown in FIG. 6, when the cell 13 is thus returned to its fully charged state, the conductor strips 44-45 are shorted electrically to the casing 13 and an electrical short thus occurs across wires 42. As previously noted, this occurrence represents a control indication of battery state-of-charge and is used here to control the recharge control switch function 22 to disconnect the recharging current to the rechargeable cell 13. Preferably, the chamber 41 between the casing 13 and the stiffener plate 40 is hermetically sealed to prevent the infusion of foreign matter which might interfere with proper switch operation. As previously mentioned, the spacing between the upper surface of the casing portion 13a and the conductor strip 44 is preselected so that contact therebetween indicates when the rechargeable cell has been returned to its fully charged condition, so that the recharge control circuitry may be operated to decrease the recharging current.

From the foregoing disclosure, it should be clear that the present invention provides a switch structure capable of sensing when a rechargeable battery or cell has been recharged to its fully charged condition by detecting deflection of the cell casing which occurs, as a result of increased internal gaseous pressure, when the cell has been returned to a fully charged state. It should furthermore be noted that this sensing has been performed while maintaining the integrity of the cell casing; e.g. no vent hole is required to sense the internal pressure of the cell. This obviously is desirable in that the cell remains hermetically sealed and is thus rendered better suited for applications wherein the cell supplies operating energy to implantable biomedical systems such as cardiac pacemakers and human tissue stimulators.

Various modifications, adaptations and alterations to the present invention are of course possible in light of the above teachings. It should therefore be understood at this time that within the scope of the apended claims, the invention may be practiced otherwise than was specifically described hereinabove.

What is claimed is:

1. In combination with a rechargeable battery of the type employed for supplying operating energy to implantable biomedical electronic apparatus, said rechargeable battery being enclosed in a hermetically sealed casing fabricated of electrically conductive material and being operably connected to receive while implanted recharging current from recharging circuitry, said rechargeable battery further being of the type which produces an increased gaseous pressure within said casing when said battery in its fully charged condition,
a switch structure for sensing state of charge of said rechargeable battery, said switch structure comprising:
an integral wall portion of said electrically conductive battery casing which deflects outwardly in response to said increased gaseous pressure,
an insulative support means secured to said electrically conductive battery casing adjacent said deflecting integral wall portion thereof, and
an electrically conductive contact means carried on said support member insulated electrically and spaced by a predetermined distance from said electrically conductive battery casing adjacent said deflecting wall portion,
said predetermined distance being selected so that said electrically conductive casing comes into electrical contact with said contact means upon outward deflection of the wall portion when said battery is returned to a fully charged state during recharging operation.

2. The combination specified in claim 1 wherein the deflecting integral wall portion of said battery casing has a reduced thickness relative to the remainder of said battery casing.

3. The combination specified in claim 2 wherein
said reduced thickness integral wall portion is formed as a recess within an external surface of said battery casing, at a predetermined location thereon,
said support means comprises an insulator member mounted on the external surface of said casing adjacent said recess, and
said electrical contact means is carried by said insulator member electrically insulated from said battery casing,
said contact means being disposed in opposed relationship to said recessed casing portion and being spaced therefrom by a predetermined distance selected so that electrical contact occurs between said recessed casing portion and said contact means when said casing portion deflects outwardly when said battery is returned to a fully charged state during a recharging operation.

4. The combination specified in claim 3 wherein said switch structure further comprises:
a plate member overlying the external surface of said casing adjacent said recessed casing portion and defining a chamber communicating with said recessed casing portion, an electrical contact member carried by said plate member and electrically insulated from said casing, said contact member being disposed in opposed relationship to said recessed casing portion and being spaced from the lower wall portion of the recess by a predetermined distance selected so that electrical contact occurs between said lower wall portion of the recess and said contact member when the reduced thickness casing portion formed by the recess has deflected a predetermined amount corresponding to said battery being returned to a fully charged state during a recharging operation.

5. The combination specified in claim 4 wherein the opposed surfaces of said contact member and said recessed casing portion are coated with an electrically conductive material to assure good electrical contact therebetween when said recessed casing portion has deflected said predetermined amount.

6. The combination specified in claim 4 wherein the chamber defined by said plate member and said recessed casing portion is heremetically sealed.

7. The combination specified in claim 4 wherein said plate member is fabricated of a structurally stiff metal, and further including
- a first electrical insulator pad member secured to the surface of said plate member opposed to said recessed casing portion,
- a second electrical insulator pad member secured to the surface of said battery casing adjacent the recess and extending away from said recessed casing portion towards a location where electrical connection is desired,
- an electrical conductor strip means mounted on said first insulator pad to form said electrical contact member, said conductor strip means extending to said electrical connection location and being insulated from said battery casing by said second insulator pad, and,
- circuit means for controlling said recharging circuitry connected respectively to said conductor strip means and to said battery case adjacent said connection location,
- whereby said recharging circuitry is controlled to decrease the recharging current to said battery when said conductor strip means is contacted by said battery casing upon deflection at said reduced thickness recessed casing portion.

* * * * *

UNITED STATES PATENT AND TRADEMARK OFFICE
CERTIFICATE OF CORRECTION

PATENT NO. : 4,275,739
DATED : June 30, 1981
INVENTOR(S) : Robert E. Fischell

It is certified that error appears in the above—identified patent and that said Letters Patent is hereby corrected as shown below:

Column 1, line 7, delete the phrase "NASA 5-23732 contract" and insert -- NASA Contract No. NAS5-23732 --.

Column 1, line 32, change "If" to -- It --.

Column 2, line 7, "casisng" should be --casing --.

Signed and Sealed this

Sixth Day of October 1981

[SEAL]

Attest:

Attesting Officer

GERALD J. MOSSINGHOFF

Commissioner of Patents and Trademarks